(12) United States Patent
Bentley et al.

(10) Patent No.: US 6,369,094 B1
(45) Date of Patent: Apr. 9, 2002

(54) POLYMORPHIC SALT

(75) Inventors: Arthur Bentley; Simon Arnold Howard-Field; Ronald James Ogilvie, all of County of Kent (GB)

(73) Assignee: Pfizer Inc., New York, NY (US)

( * ) Notice: Subject to any disclaimer, the term of this patent is extended or adjusted under 35 U.S.C. 154(b) by 0 days.

(21) Appl. No.: 09/664,946

(22) Filed: Sep. 19, 2000

(30) Foreign Application Priority Data

Sep. 28, 1999 (GB) ............................................. 9922963

(51) Int. Cl.$^7$ ..................... C07D 403/06; A61K 31/40
(52) U.S. Cl. ..................... 514/414; 548/468
(58) Field of Search ............. 548/408; 514/414

(56) References Cited

U.S. PATENT DOCUMENTS

| | | | |
|---|---|---|---|
| 5,545,644 A | 8/1996 | Macor et al. | 514/323 |
| 5,559,129 A | 9/1996 | Macor et al. | 514/323 |
| 5,559,246 A | 9/1996 | Macor | 548/468 |
| 5,578,612 A | 11/1996 | Macor et al. | 514/323 |
| 5,607,951 A | 3/1997 | Macor et al. | 514/323 |
| 6,110,940 A | * 8/2000 | Harding | 548/468 |
| 6,166,025 A | 12/2000 | Harding et al. | 514/264 |

* cited by examiner

Primary Examiner—Robert Gerstl
(74) Attorney, Agent, or Firm—Peter C. Richardson; Paul H. Ginsburg; Roy F. Waldron

(57) ABSTRACT

The present invention is concerned with a crystalline, polymorphic form of a compound of formula (I)

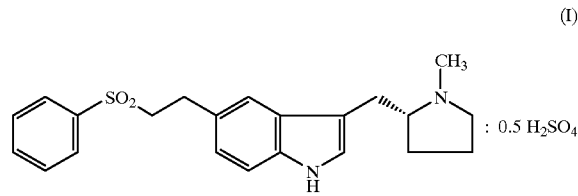

Figure 1:
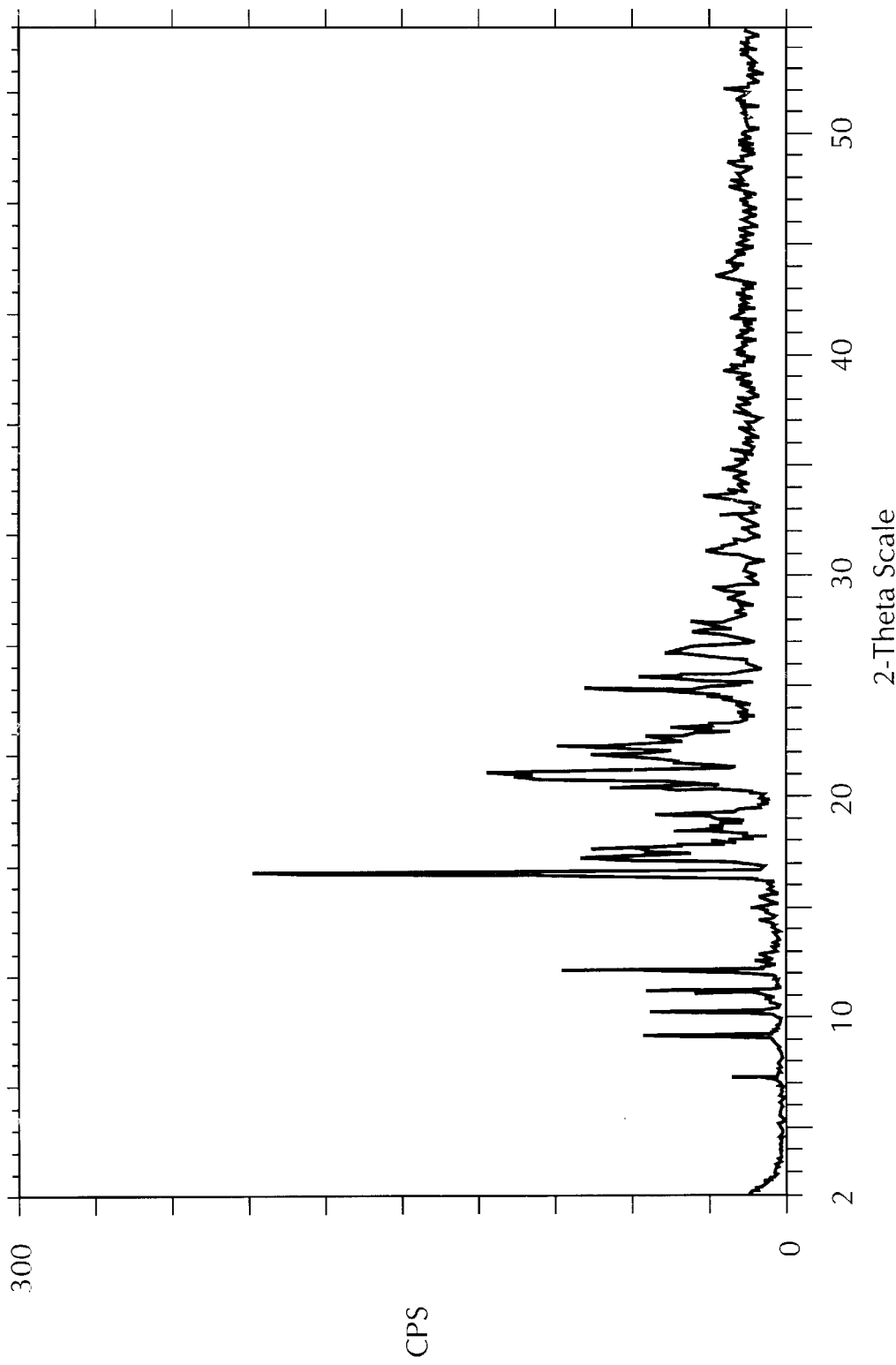

characterized by a powder X-ray diffraction pattern obtained using copper K-alpha$_1$ radiation ($\lambda$=0.15046 nm) which shows main peaks at 9.28, 10.38, 11.37, 12.40, 16.84, 17.46, 17.53, 17.78, 17.98, 19.48, 20.70, 21.29, 21.45, 22.21, 22.64, 23.08, 25.20 and 25.79.

The invention also relates to processes for the preparation of said form, to pharmaceutical compositions containing same and to its use in medicine, particularly the treatment of conditions for which an agonist of 5-HT$_1$ receptors is indicated, for example, migraine.

14 Claims, 4 Drawing Sheets

POLYMORPHIC SALT

The application claims the benefit of U.K. patent application No. 9922963.5, filed Sep. 28, 1999.

The present invention relates to the hemisulphate salt of the anti-migraine drug 3-(N-methyl-2(R)-pyrrolidinylmethyl)-5-(2-phenylsulphonylethyl)-1H-indole having formula (I):

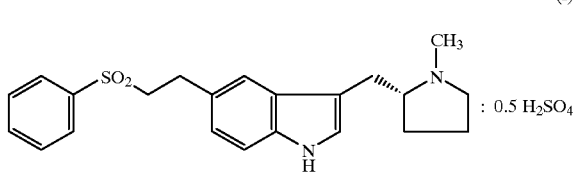

(I)

Specifically, the invention relates to a particular polymorphic form of said hemisulphate salt, to processes for the preparation of said form, to pharmaceutical compositions containing same and to its use in medicine, particularly the treatment of conditions for which an agonist of 5-$HT_1$ receptors is indicated, for example, migraine.

International Patent Application PCT/US91/07194 describes a series of 3,5-disubstituted indoles and pharmaceutically acceptable salts thereof. The hemisuccinate salt of 3-(N-methyl-2(R)-pyrrolidinylmethyl)-5-(2-phenylsulphonylethyl)-1H-indole is specifically described therein as a non-crystalline foam unsuitable for the preparation of pharmaceutical compositions, but subsequent studies indicated that the hemisulphate, hydrochloride and hydrobromide salts were all sufficiently crystalline and high-melting to be considered for this purpose.

Thus European Patent 0776323 is concerned with specific polymorphic forms of the corresponding hydrobromide salt and describes for the purposes of comparison two polymorphs of the hemisulphate salt which are referred to therein as the α- and β-forms. In contrast to the polymorphs of the hydrobromide salt, the α- and β-polymorphs of the hemisulphate salt are variously described as hygroscopic, polymorphically unstable and giving rise to colour change and punch filming during tabletting. In short, the hemisulphate polymorphs described in '323 were considered unsuitable for the preparation of solid dosage forms.

International Patent Application PCTI/EP98/04176 is concerned with aqueous pharmaceutical compositions comprising the preferred hydrobromide polymorph identified in '323 and describes for the purposes of comparison the preparation of a corresponding hemisulphate composition. The hemisulphate salt used for the preparation of said composition is the β-polymorph described in '323.

We have now unexpectedly found that there exists a third polymorph of the hemisulphate salt of 3-(N-methyl-2(R)-pyrrolidinylmethyl)-5-(2-phenylsulphonylethyl)-1H-indole which overcomes the disadvantages associated with the α- and β-forms described in European Patent 0776323. Furthermore, it has advantages over the preferred polymorph of the corresponding hydrobromide salt in terms of liquid dosage preparation.

Thus the problem addressed by the present invention is to provide a pharmaceutically acceptable hemisulphate salt of 3-(N-methyl-2(R)-pyrrolidinylmethyl)-5-(2-phenylsulphonylethyl)-1H-indole which may be efficiently processed to provide stable and effective pharmaceutical compositions, particularly those in solid or liquid dosage form. Important criteria to be satisfied are, inter alia, that the selected salt should be crystalline, non-hygroscopic and compressible, possess solid-state stability, be of suitable melting point and have acceptable solubility characteristics.

As indicated, this problem has been solved by the surprising finding of a novel polymorphic form of the hemisulphate salt of 3-(N-methyl-2(R)-pyrrolidinylmethyl)-5-(2-phenylsulphonylethyl)-1H-indole which meets the foregoing requirements, overcomes the disadvantages associated with the α- and β-polymorphs described in European Patent 0776323 and has advantages with regard to solubility and the ability to prepare liquid dosage forms over the preferred polymorph of the corresponding hydrobromide salt.

Thus according to the present invention, there is provided a crystalline, polymorphic form of a compound of formula (I) characterised by a powder X-ray diffraction (PXRD) pattern having main peaks at 9.28, 10.38, 11.37, 12.40, 16.84, 17.46, 17.53, 17.78, 17.98, 19.48, 20.70, 21.29, 21.45, 22.21, 22.64, 23.08, 25.20 and 25.79.

The polymorph of the invention is further characterised by its infrared (IR) spectrum which shows significant absorption bands at υ=3385.3, 3172.0, 3143.8, 3058.0, 3022.6, 2954.8, 2928.3, 2893.5, 2650.7, 2436.4, 1622.6, 1584.1, 1480.8, 1445.6, 1362.4, 1354.4, 1304.8, 1246.0, 1229.9, 1164.3, 1149.6, 1137.5, 1087.1, 1071.7, 1019.5, 958.9, 929.8, 899.1, 878.9, 842.6, 793.8, 759.3, 751.4, 731.3, 690.4, 619.9, 606.3, 564.9, 533.7, 512.2, 503.6, 485.3, 457.5 and 428.9 $cm^{-1}$.

The polymorph of the invention is yet further characterised by its Differential Scanning Calorimetry (DSC) trace which shows a sharp endotherm at 226° C. corresponding to its melting point.

In marked contrast to the α- and β-polymorphs, the hemisulphate polymorph of the present invention shows negligible hygroscopicity, no change in its polymorphic form after seven months as demonstrated by Powder X-Ray Diffraction (PXRD) and Differential Scanning Calorimetry (DSC) and no significant colour change or punch filming upon compression. At pH 4.0, the polymorph of the invention has a solubility very similar to that of the preferred hydrobromide of '323, but at the more biologically significant pH 6.0 its solubility increases to 478 mg/ml compared to 2.90 mg/ml for the hydrobromide.

The foregoing properties render the polymorph of the invention eminently suitable for the preparation of pharmaceutical compositions, particularly those in solid or liquid dosage form. Thus, according to a further aspect of the present invention, the polymorph of the invention and pharmaceutical compositions thereof are provided for use as medicaments.

The present invention also provides processes for the preparation of said polymorph, either in a single solvent or by reprocessing the initially-formed product in a different solvent. Reprocessing typically takes the form of refluxing the initially-formed product in a different solvent followed by isolation of the desired polymorph.

The polymorph of the invention may, for example, be obtained by (i) treatment of a solution of 3-(N-methyl-2(R)-pyrrolidinylmethyl)-5-(2-phenylsulphonylethyl)-1H-indole in a first suitable solvent, for example, acetone or tetrahydrofuran, with concentrated sulphuric acid, typically at a temperature of from −2 to 2° C., followed by heating under reflux in the same solvent; or by (ii) treatment of a solution of 3-(N-methyl-2(R)-pyrrolidinylmethyl)-5-(2-phenylsulphonylethyl)-1H-indole in a first suitable solvent, typically acetone, with concentrated sulphuric acid, typically at a temperature of from −2 to 2° C., followed by isolation of the resulting slurry and reprocessing in a second suitable solvent, for example, tetrahydrofuran.

In both cases, the resulting solution is cooled and the desired polymorph isolated. Seeding may be employed to induce crystallisation, but this is usually unnecessary.

According to a further aspect of the present invention, there are provided pharmaceutical compositions comprising the hemisulphate polymorph of the invention together with a pharmaceutically acceptable excipient, diluent, or carrier.

Thus the compound of the invention may be administered alone, but will generally be administered in admixture with a suitable pharmaceutical excipient, diluent, or carrier selected with regard to the intended route of administration and standard pharmaceutical practice.

For example, the compound of the invention may be administered orally, buccally, or sublingually in the form of optionally flavoured and/or coloured tablets, capsules, ovules, elixirs, solutions, or suspensions suitable for immediate, delayed, or controlled release applications. The compound may also be administered by intracavernosal injection.

Such tablets may contain excipients, such as microcrystalline cellulose, lactose, sodium citrate, calcium carbonate, dibasic calcium phosphate, or glycine, disintegrants, such as starch (preferably corn, potato, or tapioca starch), sodium starch glycollate, croscarmellose sodium or certain complex silicates, and granulation binders such as polyvinylpyrrolidone, hydroxypropylmethylcellulose (HPMC), hydroxypropylcellulose (HPC), sucrose, gelatin, or acacia. Additionally, lubricating agents, such as magnesium stearate, stearic acid, glyceryl behenate, or talc may be included.

Solid compositions of a similar type may also be employed as fillers in gelatin capsules. Preferred excipients in this regard include lactose, starch, a cellulose, milk sugar, or a high molecular weight polyethylene glycol. For aqueous suspensions and/or elixirs, the compound may be combined with various sweetening or flavouring agents, colouring matter or dyes, with emulsifying and/or suspending agents and with diluents, such as water, ethanol, propylene glycol, or glycerin, or combinations thereof.

The compound may also be administered parenterally, for example, intravenously, intra-arterially, intraperitoneally, intrathecally, intraventricularly, intrastemally, intracranially, intramuscularly, or subcutaneously, or it may be administered by infusion techniques. It is best used in the form of a sterile aqueous solution which may contain other substances, for example, enough salts or glucose to make the solution isotonic with blood. If necessary, the aqueous solutions may be suitably buffered, preferably to a pH of from 3 to 9. The preparation of suitable parenteral formulations under sterile conditions is readily accomplished by standard pharmaceutical techniques well known to those skilled in the art.

For oral and parenteral administration to human patients, the daily dosage level of the compounds of the formula (I) will usually be from 0.01 mg to 20 mg/kg (in single or divided doses).

Thus tablets or capsules of the compound of the invention may contain from 0.5 mg to 0.5 g of active compound for administration either singly or two or more at a time as appropriate. The physician in any event will determine the actual dosage which will be most suitable for any individual patient and it may vary with the age, weight and response of the particular patient. The above dosages are exemplary of the average case. There can, of course, be individual instances where higher or lower dosage ranges are merited and such are within the scope of this invention.

The compound of the invention may also be administered intranasally or by inhalation and is conveniently delivered in the form of a dry powder inhaler or an aerosol spray presentation from a pressurised container, pump, spray, or nebuliser using a suitable propellant, for example, dichlorodifluoromethane, trichlorofluoromethane, dichlorotetrafluoroethane, a hydrofluoroalkane, such as 1,1,1,2-tetrafluoroethane (HFA 134A™ or 1,1,1,2,3,3,3-heptafluoropropane (HFA 227EA™, carbon dioxide, or other suitable gas. In the case of a pressurised aerosol, the dosage unit may be determined by providing a valve to deliver a metered amount. The pressurised container, pump, spray, or nebuliser may contain a solution or suspension of the active compound, for example, by using a mixture of ethanol and the propellant as the solvent, which may additionally contain a lubricant, for example, sorbitan trioleate. Capsules and cartridges (made, for example, from gelatin) for use in an inhaler or insufflator may be formulated to contain a powder mix of the compound and a suitable powder base such as lactose or starch.

Aerosol or dry powder formulations are preferably arranged so that each metered dose or 'puff' contains from 25 µg to 10 mg of a compound of the formula (I) for delivery to the patient. The overall daily dose with an aerosol will be in the range of from 100 µg to 10 mg which may be administered in a single dose or, more usually, in divided doses throughout the day.

Alternatively, the compound of the invention may be administered in the form of a suppository or pessary or it may be applied topically in the form of a lotion, solution, cream, ointment, or dusting powder. The compound may also be administered transdermally, for example, by means of a skin patch, or by the ocular route.

For ocular administration, the compound may be formulated as micronised suspensions in isotonic, pH-adjusted, sterile saline or, preferably, as solutions in isotonic, pH-adjusted, sterile saline, optionally in combination with a preservative, such as a benzylalkonium chloride. Alternatively, it may be formulated in an ointment, such as petrolatum.

For topical application to the skin, the compound of the invention may be formulated as a suitable ointment containing the active compound suspended or dissolved in, for example, a mixture with one or more of the following: mineral oil, liquid petrolatum, white petrolatum, propylene glycol, polyoxyethylene polyoxypropylene compound, emulsifying wax, or water. Alternatively, it may be formulated as a suitable lotion or cream, suspended or dissolved in, for example, a mixture of one or more of the following: mineral oil, sorbitan monostearate, a polyethylene glycol, liquid paraffin, polysorbate 60, cetyl esters wax, cetearyl alcohol, 2-octyldodecanol, benzyl alcohol, or water.

Particularly preferred compositions in accordance with the invention include conventional, controlled release and fast dispersion tablets and intranasal and intravenous solutions, all of which may readily be prepared by conventional means using the polymorph of the invention.

Finally, the invention provides for the use of the hemisulphate polymorph of the invention for the manufacture of a medicament for the curative or prophylactic treatment of a medical condition for which an agonist of 5-HT$_1$ receptors is indicated and for a method of curative or prophylactic treatment of a medical condition for which an agonist of 5-HT$_1$ receptors is indicated which comprises the administration of a therapeutically effective amount of the hemisulphate polymorph of the invention. Such conditions include migraine and associated conditions such as cluster headache, chronic paroxymal hemicrania and headache associated with a vascular disorder, depression, anxiety, an eating disorder, obesity, drug abuse, hypertension and emesis.

The preparation of the hemisulphate polymorph of the invention and pharmaceutical compositions thereof is illustrated by the following Examples.

EXAMPLE 1

A solution of 3-(N-methyl-2(R)-pyrrolidinylmethyl)-5-(2-phenylsulphonylethyl)-1H-indole (14 g) in acetone (221 ml) heated to reflux was treated with a solution of 98% sulphuric acid (1.795 g) in acetone (59 ml) adding this acid solution dropwise over 50 minutes. The resulting slurry was stirred at reflux for 2 hours, then cooled to 0° C. during 1 hour, then collected by filtration, washed with acetone (42 ml) and dried in vacuo (14.74 g). The isolated salt showed a single DSC endotherm at 226° C. consistent with the desired polymorph.

EXAMPLE 2

A solution of 3-(N-methyl-2(R)-pyrrolidinylmethyl)-5-(2-phenylsulphonylethyl)-1H-indole (14 g) in tetrahydrofuran (100 ml) cooled in an ice-bath was treated with a solution of 98% sulfuric acid (1.795 g) in tetrahydrofuran (35 ml) adding this acid solution in aliquots over approximately 1 hour. The resulting mixture was warmed to room temperature, diluted with further tetrahydrofuran (60 ml), then heated to reflux and maintained at this temperature overnight. The resulting slurry was chilled in an ice-bath and slurried for 30 minutes, then filtered, washed with tetrahydrofuran (20 ml) and dried in vacuo (15.28 g). The isolated salt showed a single DSC endotherm at 226° C. consistent with the desired polymorph.

EXAMPLE 3

3-(N-methyl-2(R)-pyrrolidinylmethyl)-5-(2-phenylsulphonylethyl)-1H-indole (344.3 g, 0.9 mol) was dissolved in acetone (4 L) and filtered, washing with acetone (2.89 L). Sulphuric acid (43.8 g, 0.438 mol) was added to the solution at −2 to 2° C. A granular slurry was formed. This material was filtered, washing with acetone (2×350 ml) to produce hemisulphate of mixed morphology (381.5 g, 98%). The salt was dried, ground in a mortar and then 370 g reslurried in refluxing tetrahydrofuran (2.96 L) for 20 hours. The mixture was cooled and filtered, washed with tetrahydrofuran (200 ml) and dried in vacuo at 50° C. (361 g, 97.6%). The isolated salt showed a single DSC endotherm at 226° C. and an IR spectrum (KBr disc) consistent with the desired polymorph.

EXAMPLE 4

The hemisulphate of mixed morphology obtained by the method of Example 3 (1.5 g) was slurried in refluxing ethanol (30 ml) for 23 hours. The mixture was cooled, then filtered, washing with ethanol (1 ml) and dried in vacuo at 50° C. The isolated salt showed a single DSC endotherm at 226° C. consistent with the desired polymorph.

EXAMPLE 5

The hemisulphate of mixed morphology obtained by the method of Example 3 (1.5 g) was slurried in refluxing isopropanol (30 ml) for 23 hours. The mixture was cooled, then filtered, washing with isopropanol (1 ml) and dried in vacuo at 50° C. The isolated salt showed a single DSC endotherm at 226° C. consistent with the desired polymorph.

EXAMPLE 6

The hemisulphate of mixed morphology obtained by the method of Example 3 (1.5 g) was slurried in refluxing Industrial Methylated Spirit (30 ml) for 23 hours. The mixture was cooled, then filtered, washing with IMS (1 ml) and dried in vacuo at 50° C. The isolated salt showed a single DSC endotherm at 226° C. consistent with the desired polymorph.

EXAMPLE 7

| Tablets for Oral Administration | |
| --- | --- |
| A. Direct Compression | mg/tablet |
| Active ingredient | 24.24 |
| Microcrystalline cellulose Ph Eur | 50.00 |
| Lactose Ph Eur | 121.76 |
| Croscarmellose sodium NF | 2.00 |
| Magnesium stearate Ph Eur | 2.00 |

The active ingredient is sieved and blended with the other components. The resultant mix is compressed into tablets using a rotary tablet press (Manesty Betapress) fitted with 6 mm normal concave punches. The resultant tablets may be film-coated with an appropriate film-coating material.

| B. Wet Granulation | mg/tablet |
| --- | --- |
| Active ingredient | 48.48 |
| Lactose Ph Eur | 64.02 |
| Maize starch Ph Eur | 21.00 |
| Polyvinylpyrrolidone (5% w/v soln) | 7.50 |
| Croscarmellose sodium NF | 7.50 |
| Magnesium stearate Ph Eur | 1.50 |

The polyvinylpyrtolidone is dissolved in purified water to an appropriate concentration. The active ingredient is sieved and blended with all of the other components except the magnesium stearate. Suitable volumes of the polyvinylpyrrolidone solution are added and the powders granulated. After drying, the granules are screened and blended with the magnesium stearate. The granules are then compressed into tablets using suitable diameter punches.

Tablets of other strengths may be prepared by altering the ratio of active ingredient to excipients or the compression weight and using punches to suit.

EXAMPLE 8

| Controlled Release Tablet | mg/tablet |
| --- | --- |
| Active ingredient | 48.48 |
| Lactose Ph Eur | 49.52 |
| Hydroxypropyl methyl cellulose Ph Eur | 100.00 |
| Magnesium stearate Ph Eur | 2.00 |

The active ingredient is sieved and blended with the other components. The resultant mix is compressed into tablets using a rotary tablet press (Manesty Betapress) fitted with 8 mm normal concave punches. The resultant tablets may be film-coated with an appropriate film-coating material.

EXAMPLE 9

| Fast Dispersion Tablet | mg/tablet |
|---|---|
| Active ingredient | 24.24 |
| Gelatin Ph Eur | 3.44 |
| Mannitol Ph Eur | 2.50 |
| Aspartame Ph Eur | 0.31 |

EXAMPLE 10

| Capsules | mg/capsule |
|---|---|
| Active ingredient | 18.18 |
| Lactose Ph Eur | 208.89 |
| Maize starch Ph Eur | 69.63 |
| Colloidal anhydrous silica Ph Eur | 0.30 |
| Magnesium stearate Ph Eur | 3.00 |
| Fill weight | 300.00 |

The active ingredient is sieved and blended with the other components. The mix is filled into size No. 2 hard gelatin capsules using suitable machinery. Other doses may be prepared by altering the fill weight and, if necessary, changing the capsules size to suit.

EXAMPLE 11

| Sublingual Tablets | mg/tablet |
|---|---|
| Active ingredient | 1.21 |
| Lactose Ph Eur | 25.00 |
| Maize starch Ph Eur | 25.00 |
| Mannitol Ph Eur | 25.00 |
| Croscarmellose sodium NF | 3.00 |
| Magnesium stearate Ph Eur | 0.80 |

The active ingredient is sieved through a suitable sieve, blended with the excipients and compressed using suitable punches. Tablets of other strengths may be prepared by altering either the ratio of active ingredients to excipients or the compression weight and using punches to suit.

EXAMPLE 12

| Intranasal Solution | mg/ml |
|---|---|
| Active ingredient | 60 |
| Glycerol | 5 |
| Absorbic acid | 0.5 | pH of formulation adjusted to from 4.0 to 5.0, preferably about pH 4.5, using aqueous sodium hydroxide solution.

EXAMPLE 13

| Intravenous Solution | mg/ml |
|---|---|
| Active ingredient | 10 |
| Sodium chloride | 9 | pH of formulation adjusted to about pH 6.0 using aqueous sodium hydroxide solution.

Characterisation by PXRD, IR and DSC Analysis (a) PXRD

The PXRD pattern was obtained using a Siemens D5000 diffractometer fitted with an automatic sample changer, a theta-theta goniometer, automatic beam divergence slits, a secondary monochromator and a scintillation counter. The sample was prepared for analysis by packing the powder sample into a 12 mm diameter, 0.25 mm deep cavity that had been cut into a silicon wafer specimen mount. The specimen was rotated whilst being irradiated with copper K-alpha$_1$ radiation ($\lambda$=0.15046 nm) with the X-ray tube operated at 40 kV/40 mA. The analysis was performed with the goniometer running in continuous-scan mode set for a 5-second count per 0.02° step over a 2-theta range of 2° to 55°. For identification of the main peaks (degree 2θ) seen in each pattern (FIG. 1 wherein 'P226' is the polymorph of the invention and 'CPS' is Counts Per Second), vide supra.

(b) IR Spectroscopy

Figure 2:
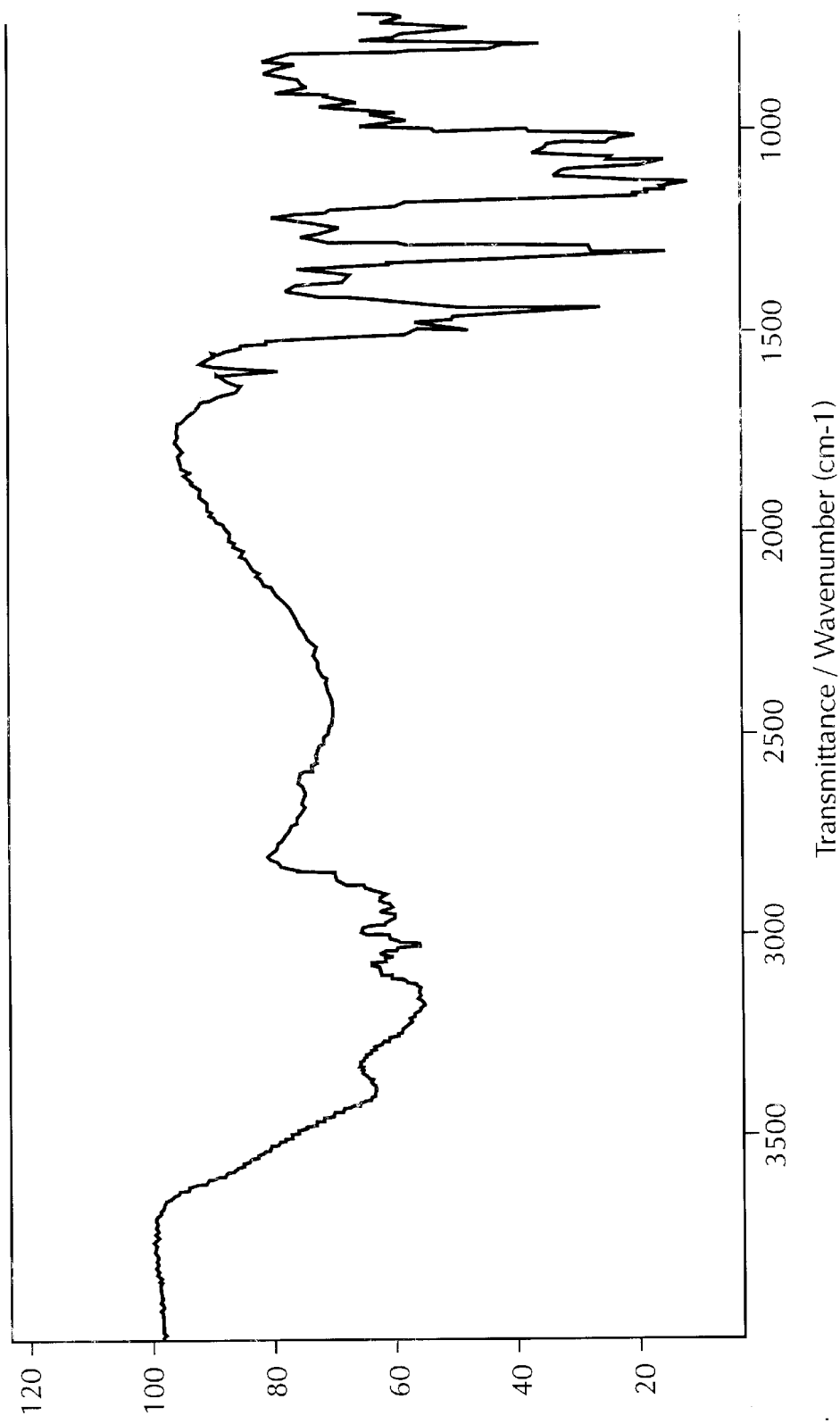

The IR spectrum was determined over the wave number ($\upsilon$) range 4000 to 400 cm$^{-1}$ using a Nicolet 800 FT-IR spectrometer fitted with a d-TGS detector. The spectrum was acquired at 2 cm$^{-1}$ resolution from a KBr disc preparation of the sample. For identification of the $\upsilon$ values of significant absorption bands (FIG. 2 wherein 'P226' is the polymorph of the invention), vide supra.

(c) Differential Scanning Calorimetry

Figure 3:
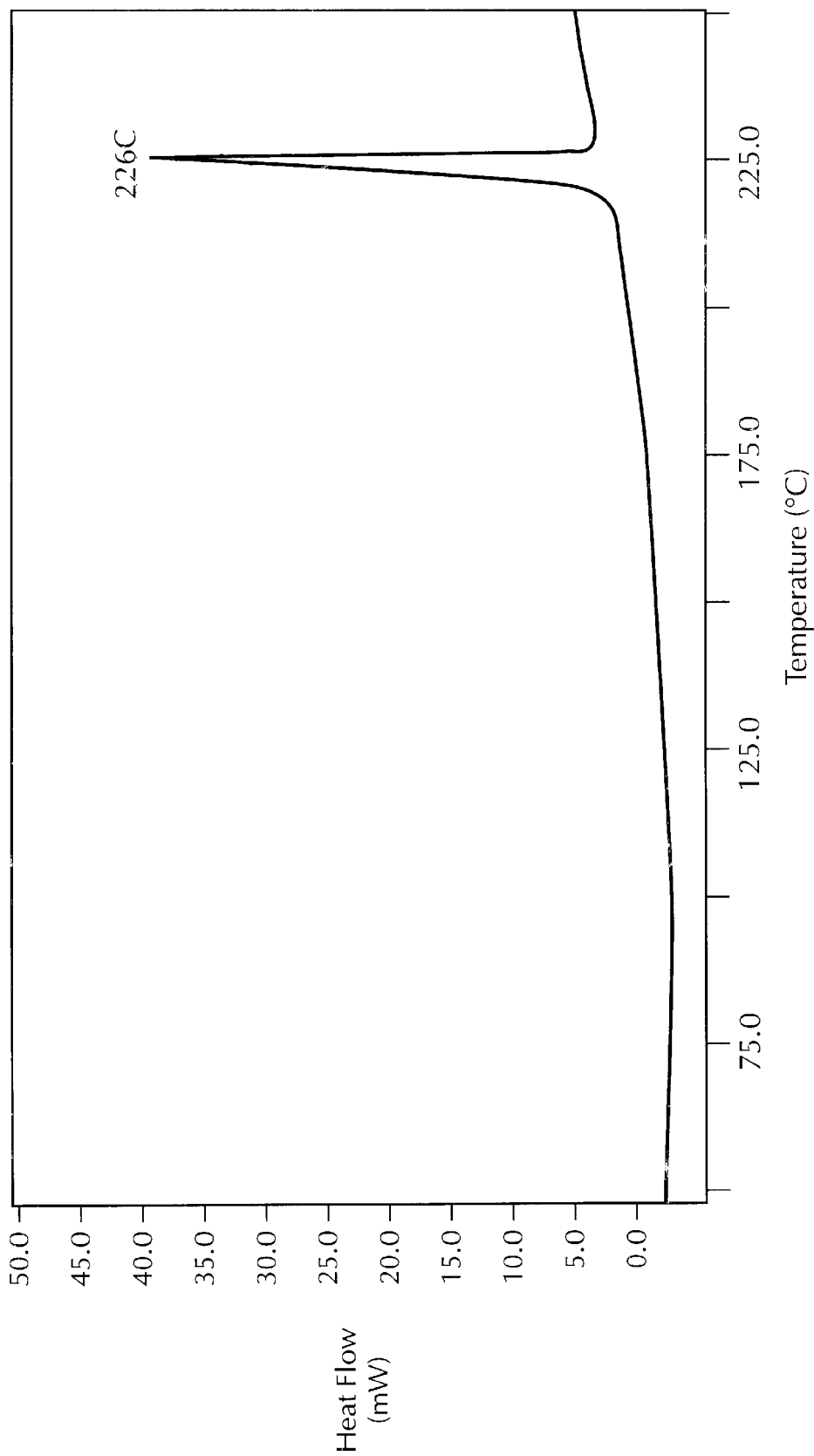

A sample (ca. 3 mg) of P226 was analysed using a Perkin Elmer DSC7 with a TAC7/DX thermal analyser controller at a scanning rate of 20° C. per minute over the range 25° C. to 300° C. For identification of the endotherm (FIG. 3 wherein 'P226' is the polymorph of the invention), vide supra.

Hugroscopicity Study

The moisture sorptions of the three known polymorphs ($\alpha$-form, $\beta$-form and present invention) of the hemisulphate of 3-(N-methyl-2(R)-pyrrolidinylmethyl)-5-(2-phenylsulphonylethyl)-1H-indole were determined using a Dynamic Vapour Sorption (DVS) Automated Sorption Analyser Model DVS-1 manufactured by Surface Measurements Systems Ltd, UK.

Each polymorph was analysed by accurately weighing approximately 25 mg into the sample pan which was then exposed to humidities in the range 0 to 75% RH. The analysis temperature was 30° C. with a nitrogen flow rate of 200 cm$^3$ min$^{-1}$.

Figure 4:
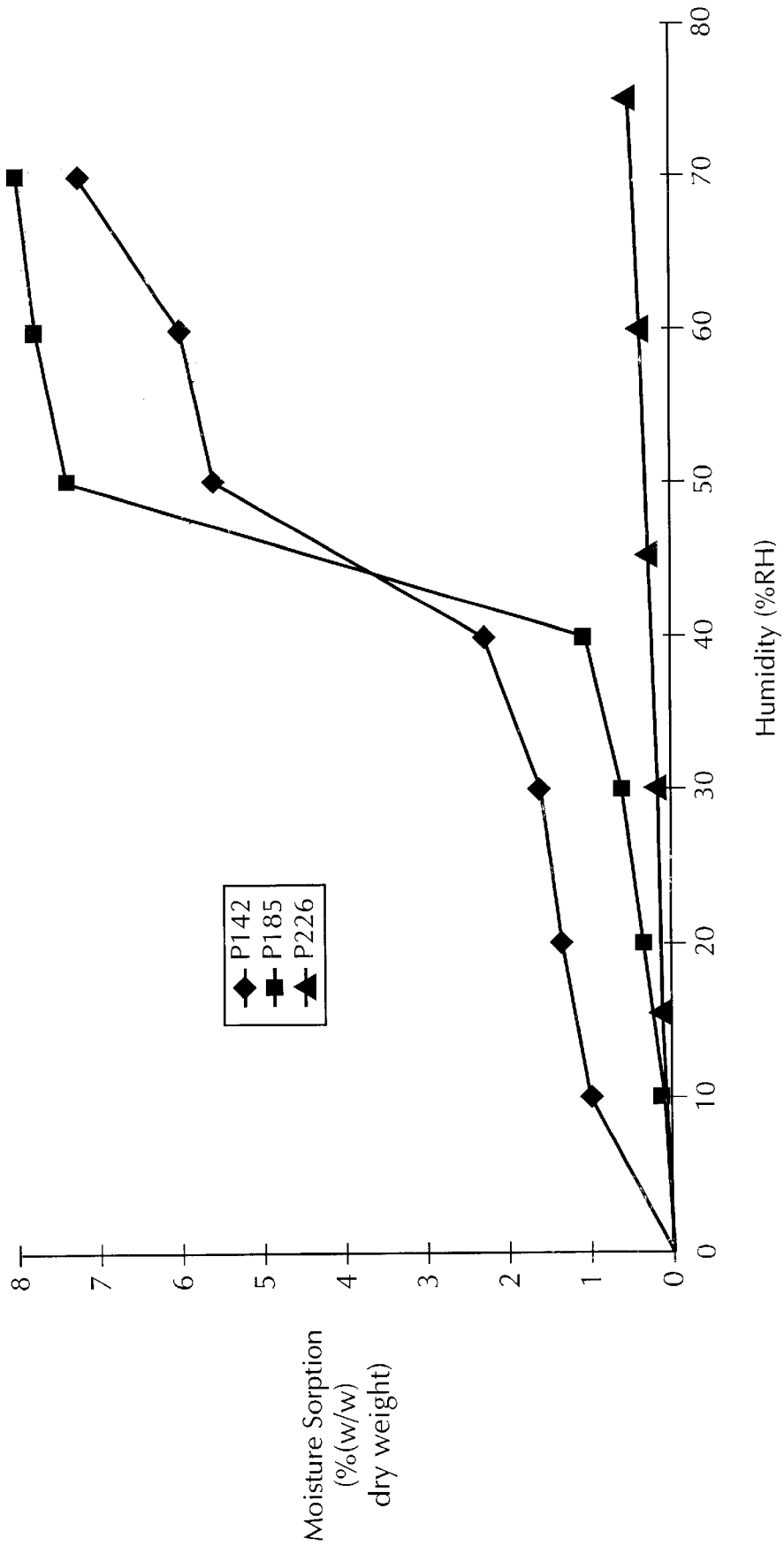

FIG. 4, wherein 'P 142' is the β-polymorph, 'P185' is the α-polymorph and 'P226' is the polymorph of the invention, illustrates the moisture sorption isotherms for the three polymorphs of the hemisulphate salt of 3-(N-methyl-2(R)-pyrrolidinylmethyl-5-(2-phenylsulphonylethyl)-1H-indole. The data shows that the polymorph of the invention is markedly less hygroscopic than either the α- or β-form, particularly above 40% RH.

Stability Study

A sample of the polymorph stored for seven months under ambient conditions was re-examined by PXRD and DSC and found to be totally unchanged, i.e. no polymorphic conversion had taken place during the period in question.

Compression Studies

Compression of a sample of the polymorph of the invention in an IR bench press (Graseby Specac Model 15.011) at a pressure of 5 tonnes for 1 minute using a 13 mm punch and die set produced no significant colour change and no evidence of punch filming.

Solubility Studies

At pH 4.0, the polymorph of the invention was found to have a solubility comparable to that of the preferred hydrobromide described in European Patent 0776323. At pH 6.0, however, solubility increased to 478 mg/ml compared to only 2.90 mg/ml for the hydrobromide.

What is claimed is:

1. A crystalline, polymorphic form of a compound of formula (I)

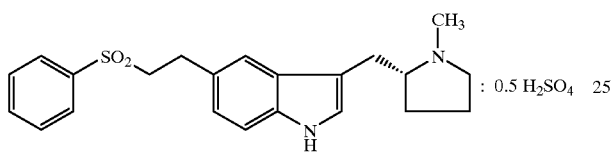

(I)

characterized by any of:
(i) a powder X-ray diffraction pattern obtained using copper K-alpha$_1$ radiation ($\lambda$=0.15046 nm) which shows main peaks at 9.28, 10.38, 11.37, 12.40, 16.84, 17.46, 17.53, 17.78, 17.98, 19.48, 20.70, 21.29, 21.45, 22.21, 22.64, 23.08, 25.20 and 25.79;
(ii) an infrared spectrum as a KBr disc which shows significant absorption bands at $v$=3385.3, 3172.0, 3143.8, 3058.0, 3022.6, 2954.8, 2928.3, 2893.5, 2650.7, 2436.4, 1622.6, 1584.1, 1480.8, 1445.6, 1362.4, 1354.4, 1304.8, 1246.0, 1229.9, 1164.3, 1149.6, 1137.5, 1087.1, 1071.7, 1019.5, 958.9, 929.8, 899.1, 878.9, 842.6, 793.8, 759.3, 751.4, 731.3, 690.4, 619.9, 606.3, 564.9, 533.7, 512.2, 503.6, 485.3, 457.5 and 428.9 cm$^{-1}$; or
(iii) a DSC trace which shows a sharp endotherm at 226° C.

2. A pharmaceutical composition comprising a compound according to claim 1 together with a pharmaceutically acceptable excipient, diluent, or carrier.

3. A pharmaceutical composition comprising a compound according to claim 1 together with a pharmaceutically acceptable excipient, diluent or carrier, and that is in solid or liquid dosage form.

4. A pharmaceutical composition according to claim 3 which is a conventional, controlled release, or fast dispersion tablet or an intranasal or intravenous solution.

5. A method of curative or prophylactic treatment of a medical condition for which an agonist of 5-HT$_1$ receptors is indicated which comprises the administration of a therapeutically effective amount of a compound according to claim 1.

6. A method according to claim 5 wherein the medical condition is migraine or an associated condition such as cluster headache, chronic paroxymal hemicrania, or headache associated with vascular disorder.

7. A method according to claim 5 wherein the medical condition is depression, anxiety, an eating disorder, obesity drug abuse, hypertension, or emesis.

8. A process for the preparation of a crystalline, polymorphic form of a compound of formula (I) according to claim 1 which comprises treatment of a solution of a compound of formula (II)

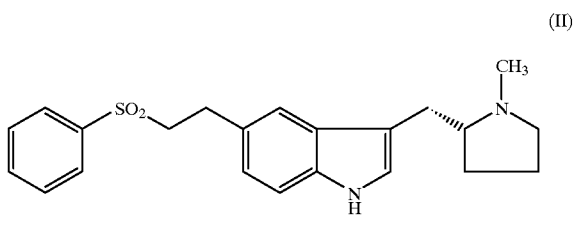

(II)

in a first suitable solvent that permits crystallization of the crystalline, polymorphic form of a compound of formula (I) with concentrated sulphuric acid, followed by either
(a) heating under reflux in the first suitable solvent that permits crystallization of the crystalline, polymorphic form of a compound of formula (I), cooling and isolating desired polymorph; or
(b) isolating the resulting slurry, taking up in second suitable solvent that permits crystallization of the crystalline, polymorphic form of a compound of formula (I), heating under reflux, cooling and isolating desired polymorph.

9. A process according to claim 8 wherein the first suitable solvent is acetone or tetrahydrofuran.

10. A process according to claim 8 wherein the first suitable solvent is acetone or tetrahydrofuran and the second suitable solvent is acetone, tetrahydrofuran, ethanol, isopropanol, or Industrial Methylated Spirit.

11. A process according to claim 8 wherein crystallization of desired polymorph is induced by seeding.

12. A process according to any of claims 8 to 10 wherein the polymorph so obtained is further characterised by its infrared spectrum as a KBr disc which shows significant absorption bands at $v$=3385.3, 3172.0, 3143.8, 3058.0, 3022.6, 2954.8, 2928.3, 2893.5, 2650.7, 2436.4, 1622.6, 1584.1, 1480.8, 1445.6, 1362.4, 1354.4, 1304.8, 1246.0, 1229.9, 1164.3, 1149.6, 1137.5, 1087.1, 1071.7, 1019.5, 958.9, 929.8, 899.1, 878.9, 842.6, 793.8, 759.3, 751.4, 731.3, 690.4, 619.9, 606.3, 564.9, 533.7, 512.2, 503.6, 485.3, 457.5 and 428.9 cm$^{-1}$.

13. A process according to claim 12 wherein the hemisulphate polymorph so obtained is further characterised by a DSC trace which shows a sharp endotherm at 226° C.

14. A parmaceutical composition according to claim 2 which is a conventional controlled release, or fast dispersion tablet or an intranasal or intravenous solution.

* * * * *